United States Patent [19]

Faucher

[11] Patent Number: 4,705,512
[45] Date of Patent: Nov. 10, 1987

[54] OSTOMY POUCH COVER

[76] Inventor: Paul W. Faucher, Box 142A, Lake Village, Ind. 46349

[21] Appl. No.: 893,393

[22] Filed: Aug. 5, 1986

[51] Int. Cl.$^4$ .............................................. A61F 5/44
[52] U.S. Cl. .................................. 604/332; 604/337; 604/339
[58] Field of Search ............... 604/51, 54, 332–345; 150/52 E; 383/7, 117, 84, 85, 119; 224/240

[56] References Cited

U.S. PATENT DOCUMENTS

| | | | |
|---|---|---|---|
| 1,441,282 | 1/1923 | Hodgson | 150/52 E |
| 2,662,525 | 12/1953 | Priebe | 604/343 |
| 4,519,797 | 5/1985 | Hall | 604/332 |

FOREIGN PATENT DOCUMENTS 469655  9/1973  Australia .............................. 383/84

OTHER PUBLICATIONS

Dictionary of Textile Terms, Dan River Inc., Danville, Va. 24541.

Primary Examiner—C. Fred Rosenbaum
Assistant Examiner—J. L. Kruter
Attorney, Agent, or Firm—Richard G. Kinney

[57] ABSTRACT

A cover for an ostomy pouch of the type which is attached to a fitting secured to the skin of a patient's abdomen. The cover is made of soft, absorbent, thin, flexible fabric and has a back panel which is secured along its sides to a front panel to form a tube section. The front panel has a flap extension at its top, formed of the same material. The tube section is drawn over and around the bottom of the pouch, so that the back panel lays flat between the user's skin and the pouch, and extends up to the fitting. The flap is drawn up and folded over the waistband of the user's underpants, to be flat in front of it, between the underpants and the user's outerwear. The flap in this manner quickly and easily holds the upward opening of the tubular section in place about the pouch, without it slipping downward, while the user may engage in normal activities, such as walking, running, reaching, etc.

10 Claims, 7 Drawing Figures

OSTOMY POUCH COVER

FIELD OF THE INVENTION

The present invention relates to a novel cover for an ostomy pouch or bag (Class 604, Subclass 332).

BACKGROUND OF THE INVENTION

In persons having intestinal problems which render all or a portion of the intestines inoperative due to disease or other pathological conditions or temporarily inoperative due to inflammation or surgery, a surgical procedure known as an ostomy is performed, in which a passageway or stoma is made through the skin typically through the abdominal wall. A portion of the intestine is re-routed and surgically connected to the stoma such that waste material can exit the body.

The term "ostomy" covers all types of surgical procedures wherein a passageway is formed through the skin and a portion of the intestine connected thereto. When a portion of the large intestine or colon is connected to the stoma or passageway, the surgical procedure is referred to as a "colostomy". When the small intestine is involved, the surgical procedure is known as an "ileostomy". Both types of procedures require an ostomy bag which is affixed to or worn on the body and is in communication with the stoma to collect waste material exiting therethrough. A wide variety of ostomy bags and methods for attaching them to the body have been previously devised.

A common type of ostomy bag which has found widespread use is formed of a plastic material and has an aperture located on one side in which a means for attaching the ostomy bag to the body is mounted so as to dispose the interior of the bag in communication with the stoma for receiving waste material exiting the body through the stoma. The bottom end of the bag is in the form of a narrow throat and has a slot formed therein. The throat is typically folded up and secured in place by a removable fastener to sealingly close the bottom of the bag, so as to retain the waste material therein and, yet, enable the bag to be opened for emptying the contents therefrom.

Although such ostomy bags effectively collect waste material, they are not without certain disadvantages. Previously devised ostomy bags are typically formed of a transparent or semi-transparent material, which renders the collected body waste material in the bag somewhat visible. Furthermore, as ostomy bags are typically formed of a plastic material, they have a tendency to stick to the body of the wearer and cause discomfort and/or skin irritation.

Covers have been previously proposed and are commercially available. See, for example, U.S. Pat. Nos. 3,089,493; 4,439,191; Des. 245,119; Des. 270,091; 4,495,662; and 4,519,797. Similar covers have been proposed for other such apertures, e.g., that shown in U.S. Pat. No. 4,173,979. Squibb through its Convatec division (P.O. Box 4000, Princeton, NJ, 08540) markets a Sur-fit TM pouch cover (Order No. 180140), and the Undercover Cover Company (P.O. Box 579, Pocatello, Id, 83204), markets a number of different types of such covers. ComfortCare Products (Box 1118, Fairfield, IA, 52556) offers a Pocket-Pouch ® Cover similar to that disclosed in the aforementioned U.S. Pat. No. 4,519,797. Despite the great deal of activity in this area, there was not, heretofore, an ostomy cover which is economical to make, easy and quick to install, and yet holds itself securely in place under the user's clothing during normal activity.

SUMMARY OF THE INVENTION

The present invention, to provide such a cover, provides a cover which is secured by means of a flexible flap which is drawn up and folded over the waistband of the user's underwear or folded over an appliance belt if one is worn. With such a flap, the covering portion, preferably a fabric tube formed of a pair of panels seamed along their edges and open at its top, can be easily slid up about the appliance pouch and the flap drawn over and folded down in front of the waistband or belt, without the need of snaps, stops, belts, or fabric pockets which must be carefully fitted over the top of the pouch and stretched over and about the ostomy fitting.

The present invention thus provides a cover which can be used easily and secured quickly. The invention cover may be made of one or two flat panels of thin fabric sewn straight along the sides, and this is also easy and economical to manufacture, with only a minimum requirement of labor.

The invention, together with further advantages thereof, may best be understood by reference to the following description taken in connection with the accompanying drawings, in the several figures of which, like reference numerals identify like elements.

DETAILED DESCRIPTION OF ONE EMBODIMENT

Figure 1:
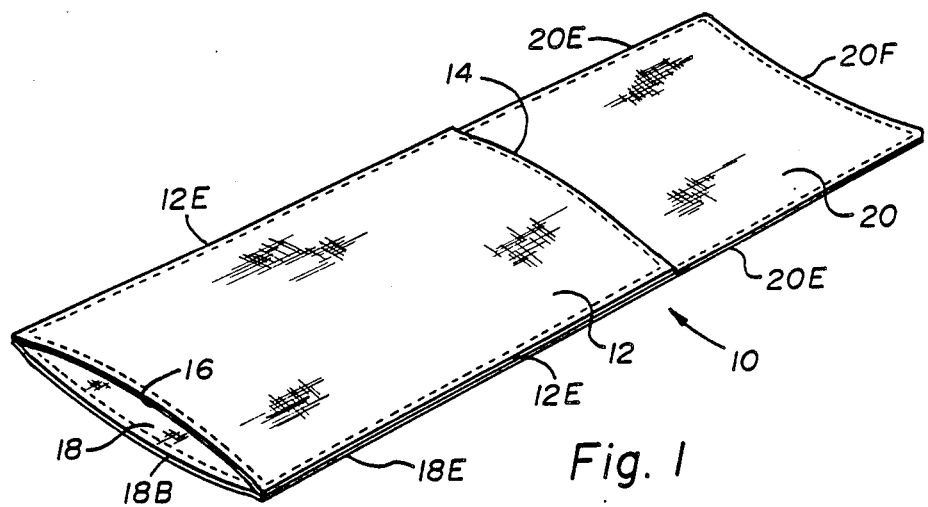
FIG. 1 is a perspective view of an ostomy pouch cover constructed in accordance with the principles of the present invention.

Referring to the drawings and initially FIG. 1, there is depicted an ostomy pouch cover constructed in accordance with the principles of the present invention and generally designated by the number 10. The cover 10 is constructed of generally flat thin sheet material and includes a back panel 12 of a generally rectangular shape. This panel 12 is made of thin absorbent fabric, such as that known in the trade as "T-Shirt" material (e.g. 50% combed cotton, 50% Dacron polyester). The panel 12 has a top edge 14 which is finished so as not to unravel or tear easily, by a locked over-edge stitch. It has a bottom edge 16 which is similarly finished. The panel 12 has a longitudinal edge designated 12E.

Figure 2:
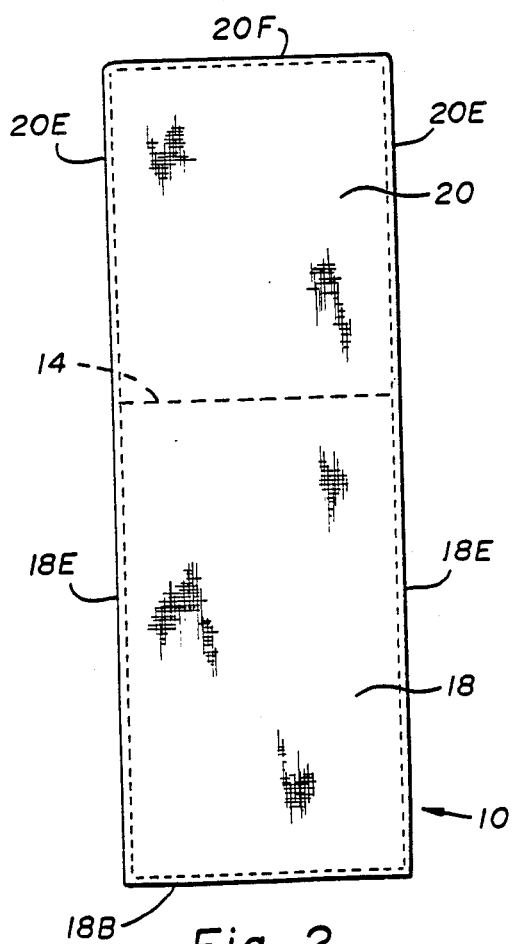
FIG. 2 is a plan view of the cover of FIG. 1.
Figure 3:
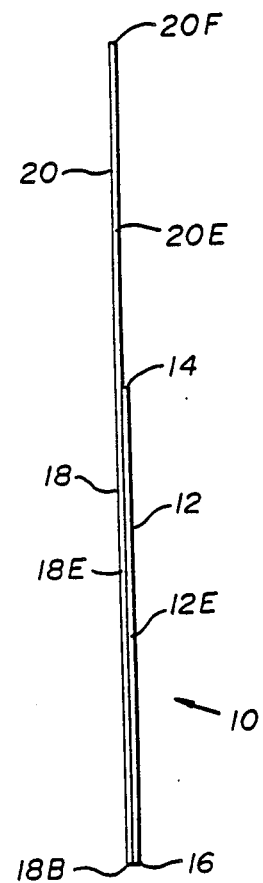
FIG. 3 is a side view of the back of the cover of FIGS. 1 and 2.

The cover 10 includes a front panel 18 which is best seen in FIG. 2. The panel 18 is sized in width to be about the same width as the panel 12 and has edges 18E which are atop the edges 12E of the panel 12. The two panels are secured together or united along these edges 12E, 18E by over-edge locked stitching.

The front panel 18 is preferably made of the same material as is the back panel 12 and has a bottom edge 18B finished as were the edges 14 and 16.

The edges 16 and 18B are preferably not sewn together or otherwise connected. The top edge 14 is not secured to the panel 18 (except at the corners). This results in a flexible tube or sleeve-like structure, open at the top and bottom.

A flap 20 of flat, flexible sheet material is provided, secured to the top of the front panel 18 and preferably may be, as shown, made unitarily therewith and of the same material. The flap 20 is generally rectangular, of the same width as the panel 18, and has its outer edges 20E and 20F finished in the same manner as the edges 14 and 16.

Figure 4:
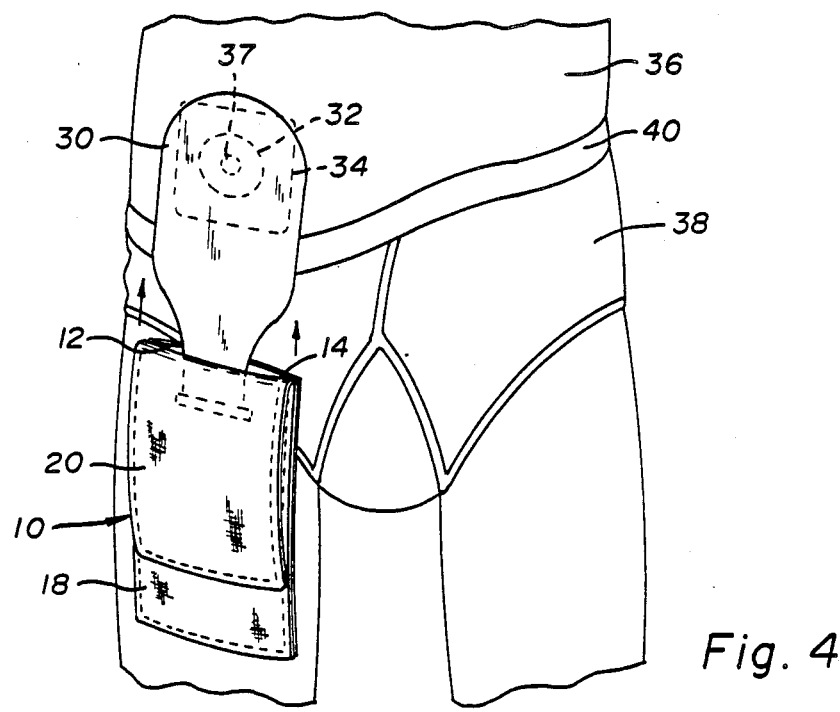
FIGS. 4–6 are each a perspective partial view of an ostomy pouch user wearing underpants and ostomy pouch together with the inventive cover of FIGS. 1–3, with hidden parts shown in dashed outline, illustrating successive steps in placing the cover onto the pouch and securing it in place.

The panels 12 and 18 are sized slightly wider than a standard ostomy pouch such as the pouch 30 shown in FIG. 4. Such pouches are secured to an appliance ring 32 of an ostomy fixture 34 which is adhesively secured to the skin of a patient or user 36 about a stoma 37 through the abdomen. The patient 36 is shown using conventional brief underpants 38 having a waistband 40.

The stomas are conventionally positioned just below the waistline and to one side of the patient 36, generally as shown, although they can vary in position and side. The bag or pouch 30 is normally under the underpants.

As shown in FIG. 4, the pouch 10 is formed so as to easily receive the pouch 30 within the flat tube or sleeve formed by the panels 12 and 18, through the top opening between those panels.

In placing the cover on the pouch 30, it is preferably placed outside of the user's underpants 38, as shown in FIG. 4, and the cover installed as shown and raised up about the bottom of the pouch 30 (as indicated by the arrows). Note the cover 10 is wide enough to surround the fixed or maximum width of the pouch 30.

Figure 5:
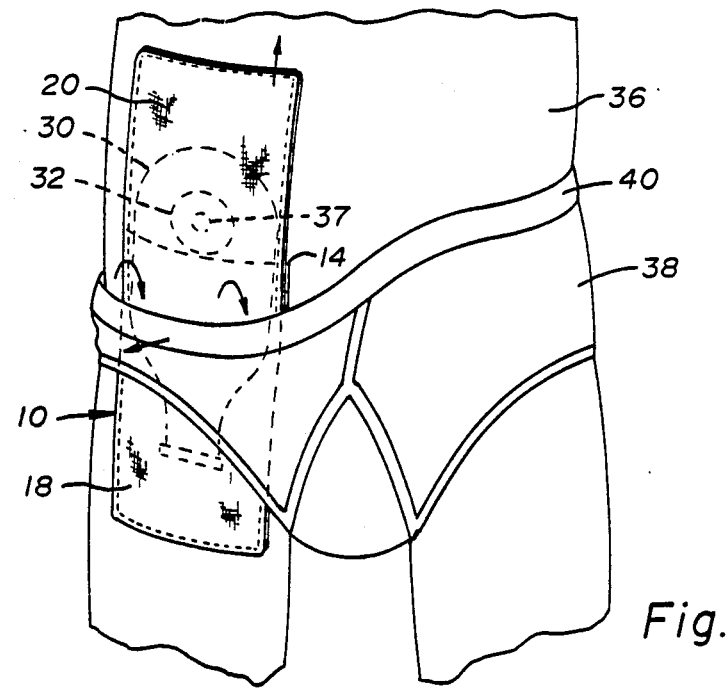
Figure 6:
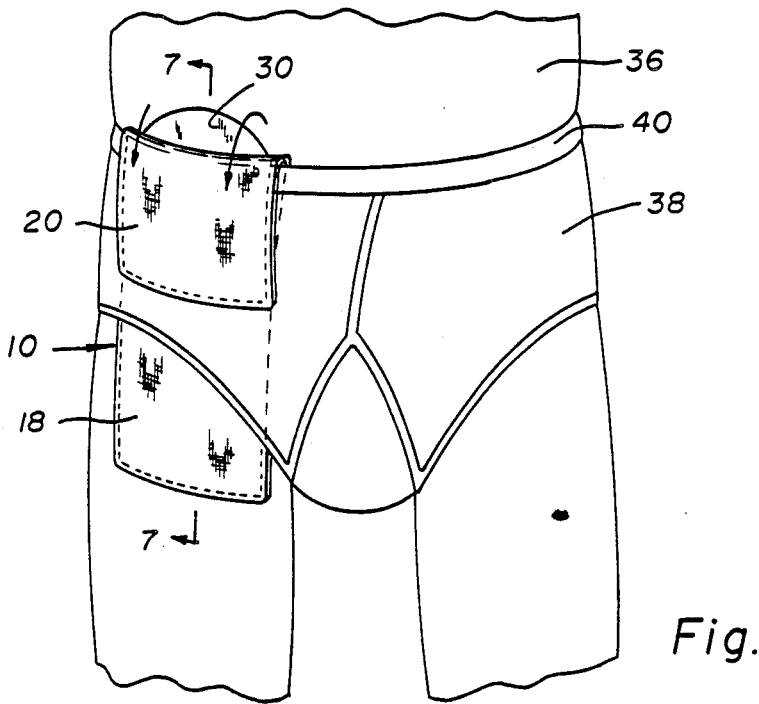
Figure 7:
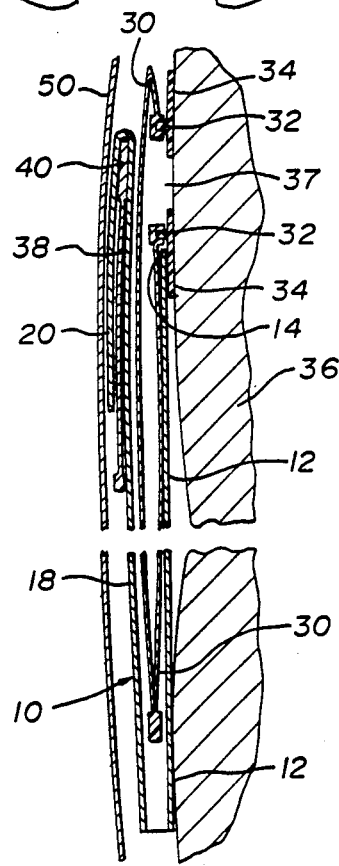
FIG. 7 is a sectional view as seen from the line 7—7 of FIG. 6, looking in the direction of the arrows, of the installed cover, pouch, and adjacent articles.

The cover 10 is drawn upward until the top edge 14 of the back panel 12 meets the underside of the ring 32, as shown in FIG. 5. The pouch and its encompassing cover portion made up of the panels 12 and 18 are then placed under the briefs 38 and, as shown in FIG. 6, the flap folded down along and over the waistband 40 of the briefs 38. In this position, the waistband 40 and briefs 38 hold the cover in place. When outer garments are worn (e.g., the garment 50 shown in FIG. 7), they aid further in holding the cover 10 in place.

Note that the length of the panel 12 is sufficient to completely reach the predetermined fixed distance between the ring 32 and the bottom of the pouch 30. While a small area of the pouch above the ring 32 is not covered, this area is already substantially shielded from the skin of the user by the fixture 34 (FIG. 4).

Prototypes constructed substantially as shown and described have been built and tested extensively and proven to be comfortable and held securely in place despite normal vigorous activity.

One such prototype was made of the material identified above, with the panel 12 being about 6 inches wide by 10 inches long. The combined panels 18 and 20 were about 6 inches wide by 17 inches long, to provide a flap panel 7 inches long.

While it is important that the back panel 12 (which bears against the skin of the user 36) be made of absorbent preferably soft fabric (such as the example given earlier), the front and flap panels 18 and 20 do not usually touch the patient's skin during wear and thus could be made of another material without departing from the broader principles of the present invention. However, for reasons of economy and ease of manufacture, the same fabric was used in the prototypes and is presently preferred. Also, although the front panel 18 is shown and is preferred to be of equal length as the back panel 12 for the same reason as before, it could be of different shapes, e.g., formed of one or a series of shorter bands between the edge 12E. And, while the rectangular shape to the flap 20 is presently preferred, it could be shaped differently and perhaps made in more than one section.

Without departing from the broader aspects of the present invention, the panels 12, 18, and 20 can also be made from a single piece of cloth, with one of the edges 12E–18E being a crease or fold. Alternatively, the tube 12–18 can be formed seamlessly, as by knitting the fabric in the manner of seamless stockings. The sewn side is preferred, to provide more definition to the cloth cover 10 and to aid in laying flat the tube formed by the front and back panels 12 and 18. And, while an opening at the bottom is preferred so as to allow free access to the pouch's bottom and its conventional resealable opening, the edges 16 and 18B can be sewn or otherwise secured together so that the panels 12 and 18 form a pocket about the pouch 30.

Some fittings such as the fitting or fixture 34 are held in place by a separate appliance belt or band. The flap 20 of the present invention may alternatively be folded over this belt or band in an area on one side or the other of the pouch 30, to hold the cover in place.

While one particular embodiment of the invention has been shown and described, it will be obvious to those skilled in the art that changes and modifications may be made without departing from the invention, and, therefore, the aim in the appended claims is to cover all such changes and modifications as fall within the true spirit and scope of the invention.

I claim:

1. An ostomy cover for an ostomy pouch of the type comprising a waterproof pouch having an opening engaging with a fitting worn by a patient under the patient's underpants having a waistband, below the waist of a patient with the pouch extending and having a bottom below that fitting, said cover comprising:

a back panel of flexible fabric; a front panel of flexible material secured to the back panel along its sides, said front and back panel thus forming a tubular structure of flexible material, which structure is open at its top and is sized to fit over the bottom of the ostomy pouch and have said back panel extend from the bottom of the fitting to or below the bottom of the pouch;

a flap means of flexible material secured at the top of said front panel and extending therefrom for a distance sufficient to allow said flap means to extend to and over and around the waistband of the patient's underpants so as to lay flat, in part, outside of the underpants;

whereby said ostomy cover is held in place by the contact between the flap means and the patient's clothing.

2. The ostomy cover of claim 1 wherein the flap means is made unitarily with the front panel and is at least approximately seven inches in length.

3. The ostomy cover of claim 2 wherein the front panel and flap means are made of the same fabric as the back panel.

4. The ostomy cover of claim 2 wherein the flap means is about 7 inches in length and six inches in width.

5. In combination, a cover and an ostomy pouch of the type having an appliance ring near its top for affixture to a stoma appliance, said pouch extendidng a predetermined fixed distance below that ring and having a fixed maximum width below that ring, the cover comprising:
  underwear having a waistbelt
    a back panel of absorbent soft fabric such as a cotton blend knit having longitudinally extending side edges, sized to span the fixed maximum width of the ostomy pouch extending length at least equal to the predetermined fixed distance;
    a front panel means having connected side edges to said side edges of said back panel and spanning between them for allowing said back panel to be positioned behind the bottom of the ostomy pouch with said front means spanning across the front of the ostomy pouch; and
    a flexible flap means connected to said front panel means and projecting upward therefrom, said flap means being of at least four inches in length and being folded back over said underwear waist belt worn with the ostomy pouch for holing said back panel in position.

6. The ostomy cover of claim 5 wherein the flap is made unitarily with the front means and is at least four inches in length.

7. The ostomy cover of claim 6 wherein the front means and flap are made of the same fabric as the back panel.

8. The ostomy cover of claim 6 wherein the flap is about 7 inches in length and six inches in width.

9. The cover of claim 7 wherein the back panel is about six by ten inches and the combined size of the front panel and flap is six by seventeen inches.

10. The method of use of an ostomy cover for covering an ostomy pouch attached to a stoma fitting of a person, which fitting is located generally below the person's waist, for a person who wears an encircling waist band about that area, said cover comprising:
  a sleeve made of flexible material having a front panel and back panel, said sleeve being sized to fit easily around an ostomy pouch when the pouch is installed on a fitting and being of a length such as to cover the bottom of the pouch, said sleeve having an outer surface of absorbent material on at least its back side, a projecting flap extension means on its front panel, said flap means being made of a flexible material and being capable of being folded transversely, comprising the steps of;
1. provide a waistband around the waist of a patient,
2. place a stoma fitting over the stoma of an ostomy patient,
3. place said ostomy bag between the front and back panels of said cover so that said flap extension means extends above the waistband and said absorbent material directly contacts the user's skin,
4. fold the flap extension means back over the waist band parallel to the back panel so that the pack panel and the flap extension means holds the ostomy pouch in place.

* * * * *

UNITED STATES PATENT OFFICE
CERTIFICATE OF CORRECTION

PATENT NO. : 4,705,512
DATED : November 10, 1987
INVENTOR(S) : Paul W. Faucher

It is certified that error appears in the above-identified patent and that said Letters Patent are hereby corrected as shown below:

Column 2 - Line 35: after "plan view of the" insert --back of the--

Column 2 - Line 36: delete "back of the"

Signed and Sealed this

Twenty-fourth Day of May, 1988

Attest:

Attesting Officer

DONALD J. QUIGG

Commissioner of Patents and Trademarks